US010188773B2

(12) United States Patent
Martin et al.

(10) Patent No.: US 10,188,773 B2
(45) Date of Patent: *Jan. 29, 2019

(54) COMPOSITIONS AND DEVICES OF POLY-4-HYDROXYBUTYRATE

(71) Applicant: Tepha, Inc., Lexington, MA (US)

(72) Inventors: David P. Martin, Arlington, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/274,422

(22) Filed: Sep. 23, 2016

(65) Prior Publication Data

US 2017/0014552 A1 Jan. 19, 2017

Related U.S. Application Data

(63) Continuation of application No. 14/529,217, filed on Oct. 31, 2014.

(60) Provisional application No. 61/900,348, filed on Nov. 5, 2013.

(51) Int. Cl.
| | | |
|---|---|---|
| *A61L 31/10* | (2006.01) | |
| *A61L 17/10* | (2006.01) | |
| *A61L 27/18* | (2006.01) | |
| *A61L 31/06* | (2006.01) | |
| *C08G 63/06* | (2006.01) | |
| *C12P 7/62* | (2006.01) | |
| *G01N 33/50* | (2006.01) | |
| *A61L 27/34* | (2006.01) | |
| *C08G 63/90* | (2006.01) | |

(52) U.S. Cl.
CPC ............ *A61L 31/06* (2013.01); *A61L 17/105* (2013.01); *A61L 27/18* (2013.01); *A61L 27/34* (2013.01); *A61L 31/10* (2013.01); *C08G 63/06* (2013.01); *C08G 63/90* (2013.01); *C12P 7/625* (2013.01); *G01N 33/5088* (2013.01); *Y10T 436/201666* (2015.01)

(58) Field of Classification Search
CPC combination set(s) only.
See application file for complete search history.

(56) References Cited

U.S. PATENT DOCUMENTS

| | | | |
|---|---|---|---|
| 5,811,272 A | 9/1998 | Snell | |
| 6,043,063 A | 3/2000 | Kurdikar | |
| 6,087,471 A | 7/2000 | Kurdikar | |
| 6,245,537 B1 | 6/2001 | Williams | |
| 6,548,569 B1 | 4/2003 | Williams | |
| 6,555,123 B2 | 4/2003 | Williams | |
| 6,585,994 B2 | 7/2003 | Williams | |
| 6,610,764 B1 | 8/2003 | Martin | |
| 6,623,748 B2 | 9/2003 | Clokie | |
| 6,828,357 B1 | 12/2004 | Martin | |
| 6,838,493 B2 | 1/2005 | Williams | |
| 6,867,247 B2 | 3/2005 | Williams | |
| 6,867,248 B1 | 3/2005 | Martin | |
| 6,878,758 B2 | 4/2005 | Signer | |
| 7,025,980 B1 | 4/2006 | Williams | |
| 7,070,966 B2 | 7/2006 | Schumann | |
| 7,098,298 B2 | 8/2006 | Kinoshita | |
| 7,118,897 B2 | 10/2006 | Narasimhan | |
| 7,179,883 B2 | 2/2007 | Williams | |
| 7,226,765 B2 | 6/2007 | Narasimhan | |
| 7,244,442 B2 | 7/2007 | Williams | |
| 7,252,980 B2 | 8/2007 | Walsem | |
| 7,268,205 B2 | 9/2007 | Williams | |
| 7,393,668 B2 | 7/2008 | Yanagita | |
| 7,435,567 B2 | 10/2008 | Osakada | |
| 7,553,923 B2 | 6/2009 | Williams | |
| 7,576,173 B2 | 8/2009 | Walsem | |
| 7,618,448 B2 | 11/2009 | Schmitz | |
| 7,641,825 B2 | 1/2010 | Rizk | |
| 8,016,883 B2 | 9/2011 | Coleman | |
| 8,034,270 B2 * | 10/2011 | Martin | A61F 2/0063 264/103 |
| 8,231,889 B2 | 7/2012 | Williams | |
| 8,287,909 B2 | 10/2012 | Martin | |
| 8,357,508 B2 | 1/2013 | Mantelatto | |
| 8,771,720 B2 | 7/2014 | Williams | |
| 9,290,612 B2 * | 3/2016 | Martin | |
| 9,480,780 B2 | 11/2016 | Martin | |
| 2004/0234576 A1 | 11/2004 | Martin | |
| 2007/0161096 A1 | 7/2007 | Mantelatto | |
| 2014/0275325 A1 * | 9/2014 | Martin | C08L 67/04 523/113 |

FOREIGN PATENT DOCUMENTS

| | | | |
|---|---|---|---|
| DE | 3937649 | 5/1991 | |
| WO | WO 9107229 A1 * | 5/1991 | ........... B02C 18/142 |
| WO | 9846783 | 10/1998 | |
| WO | 199932536 | 7/1999 | |
| WO | 200056376 | 9/2000 | |
| WO | 03068919 | 8/2003 | |
| WO | 2011100601 | 8/2011 | |
| WO | 2011119742 | 9/2011 | |
| WO | 2011159784 | 12/2011 | |
| WO | 2012064526 | 5/2012 | |
| WO | 2013023140 | 2/2013 | |

(Continued)

OTHER PUBLICATIONS

Gorenflo, et al., "Development of a process for the biotechnological production of 4-hydroxyvalerate-containing polyesters and characterization of their physical and mechanical properties", Biomacromolecules, 2:45-57 (2001).

(Continued)

*Primary Examiner* — Alicia L Otton
(74) *Attorney, Agent, or Firm* — Pabst Patent Group LLP

(57) ABSTRACT

Compositions of P4HB with high purity have been developed. The compositions are prepared by washing P4HB biomass prior to solvent extraction, and precipitating P4HB from solution. The same solvent is preferably used to wash the P4HB biomass, and as a non-solvent to precipitate the polymer from a P4HB solvent solution. The highly pure P4HB compositions are suitable for preparing implants. The implants may be used for the repair of soft and hard tissues.

22 Claims, 1 Drawing Sheet

(56) References Cited

FOREIGN PATENT DOCUMENTS

| | | |
|---|---|---|
| WO | 2013142033 | 9/2013 |
| WO | 2014078014 | 5/2014 |

OTHER PUBLICATIONS

Hori, et al., "Chemical synthesis of high molecular weight poly(3-hydroxybutyrate-co-4-hydroxybutyrate)", Polymer, 36:4703-5 (1995).
Houk, et al., "Why delta-valerolactone polymerizes and gamma-butyrolactone does not", J. Org. Chem., 73 (7), 2674-8 (2008).
Jiang, et al., "Acetone extraction of mcl-PHA from Pseudomonas putida KT2440", J. Microbiol. Meth., 67:212-9 (2006).
Martin, et al., "Medical applications of poly-4-hydroxybutyrate: a strong flexible absorbable biomaterial", Biochem. Eng. J., 16:97-105 (2003).
Moore, et al., "Chemosynthesis of bioresorbable poly(gamma-butyrolactone) by ring-opening polymerisation: a review", Biomaterials, 26:3771-82 (2005).
Russell, et al., "Investigation of the phase morphology of bacterial PHA inclusion bodies by contrast variation SANS", Physica B. Condensed Matter, 385-386(Part 2):859-61 (2006).
Steinbüchel, et al., "Diversity of bacterial polyhydroxyalkanoic acids", FEMS Microbial. Lett., 128:219-28 (1995).
Williams, et al., "Applications of PHA\s in medicine and pharmacy", Polyesters, III, 4:91-127 (2002).
Zhou, et al., "Hyperproduction of poly(4-hydroxybutyrate) from glucose by recombinant *Escherichia coli*", Microb. Cell Fact., 11:54 (2012).
International Search Report and Written Opinion for PCT/US2014/063305 dated Jan. 29, 2015.
Guidance for Industry: Pyrogen and Endotoxins Testing: Questions and Answers, http://www.fda.gov/Drugs/Guidance-ComplianceRegulatoryInformation/Guidances/default.htm, 12 pages, compliance Jun. 2012.

\* cited by examiner

COMPOSITIONS AND DEVICES OF POLY-4-HYDROXYBUTYRATE

CROSS-REFERENCE TO RELATED APPLICATIONS

This application is a continuation of U.S. Ser. No. 14/529,217, filed Oct. 31, 2014, which claims the benefit of priority to U.S. Ser. No. 61/900,348, filed on Nov. 5, 2013, the disclosure of which is incorporated herein by reference.

FIELD OF THE INVENTION

The present invention generally relates to medical devices of poly-4-hydroxybutyrate, the compositions used to produce these medical devices, and the processes used to produce these compositions. The medical devices can be used in many types of implant applications including wound management, general surgery, hernia repair, nerve repair, tissue engineering, orthopedic, craniomaxillofacial surgery, drug delivery, cardiovascular, vascular, cardiology, urology, gynecology, dental, imaging, ear, nose and throat surgery, plastic and cosmetic surgery, and oral surgery.

BACKGROUND OF THE INVENTION

Poly-4-hydroxybutyrate (P4HB) and copolymers thereof can be produced using transgenic fermentation methods, see, for example, U.S. Pat. No. 6,548,569 to Williams et al., and are produced commercially, for example, by Tepha, Inc. (Lexington, Mass.). Poly-4-hydroxybutyrate (P4HB, Tepha-FLEX® biomaterial) is a strong, pliable thermoplastic polyester that, despite its biosynthetic route, has a relatively simple structure as shown below.

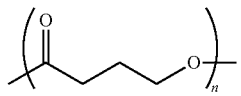

The polymer belongs to a larger class of materials called polyhydroxyalkanoates (PHAs) that are produced by numerous microorganisms (see, for example, Steinbüchel A., et al. Diversity of Bacterial Polyhydroxyalkanoic Acids, *FEMS Microbial. Lett.* 128:219-228 (1995)). In nature these polyesters are produced as storage granules inside cells, and serve to regulate energy metabolism. They are also of commercial interest because of their thermoplastic properties, biodegradability and relative ease of production.

The PHA polymers have been divided into three classes based on the number of carbon atoms in their subunits. Short-chain-length PHA polymers (or scl-PHAs) are made from monomers of 3 to 5 carbon atoms. Medium-chain-length PHA polymers (mcl-PHAs) contain 6 to 14 carbons in their monomeric units, and long-chain-length PHAs (lcl-PHAs) have monomers with more than 14 carbons. The properties of these polymers vary dramatically depending upon their chain length, including their solubilities, thermal, and mechanical properties. P4HB has four carbon atoms in its monomeric unit, and is therefore classified as a scl-PHA.

Chemical synthesis of P4HB has been attempted, but it has been impossible to produce the polymer with a sufficiently high molecular weight that is necessary for most applications (see Hori, Y., et al., *Polymer* 36:4703-4705 (1995); Houk, K. N., et al., *J. Org. Chem.,* 2008, 73 (7), 2674-2678; and Moore, T., et al., *Biomaterials* 26:3771-3782 (2005)). In fact, it has been calculated to be thermodynamically impossible to chemically synthesize a high molecular weight homopolymer under normal conditions (Moore, T., et al., *Biomaterials* 26:3771-3782 (2005)).

U.S. Pat. Nos. 6,245,537, 6,623,748, 7,244,442, and 8,231,889 describe methods of making PHAs with low levels of endotoxin. U.S. Pat. Nos. 6,548,569, 6,838,493, 6,867,247, 7,268,205, 7,179,883, 7,268,205, 7,553,923, 7,618,448 and 7,641,825 and WO 2012/064526 describe use of PHAs to make medical devices. Methods to control molecular weight of PHA polymers have been disclosed by U.S. Pat. No. 5,811,272 to Snell et al.

PHAs with controlled degradation and degradation in vivo of less than one year are disclosed by U.S. Pat. Nos. 6,548,569, 6,610,764, 6,828,357, 6,867,248, and 6,878,758 to Williams et al. and WO 99/32536 to Martin et al. Applications of P4HB have been reviewed in Williams, S. F., et al., *Polyesters, III,* 4:91-127 (2002), and by Martin, D. et al. Medical Applications of Poly-4-hydroxybutyrate: A Strong Flexible Absorbable Biomaterial, *Biochem. Eng. J.* 16:97-105 (2003). Medical devices and applications of P4HB have also been disclosed by WO 00/56376 to Williams et al. Several patents including U.S. Pat. Nos. 6,555,123, 6,585,994, and 7,025,980 describe the use of PHAs in tissue repair and engineering. U.S. Pat. Nos. 8,034,270, 8,016,883, 8,287,909, WO 2011/119742 and WO 2011/159784 disclose fibers, non-wovens, and textiles made by melt extrusion or dry spinning of P4HB.

German Patent No. DE 3937649A1 to Steinbüchel et al. discloses production of P4HB by fermentation. The P4HB polymer was identified by methanolysis of the biomass using gas chromatograpy. The P4HB polymer was not however purified from the biomass.

Two patent applications, WO 99/32536 to Martin and WO 00/56376 to Williams disclose a method to produce P4HB in recombinant *Escherichia coli* K12. The resulting biomass containing the P4HB polymer was fluidized and lyophilized, and the P4HB polymer extracted with tetrahydrofuran, filtered, precipitated, redissolved in solvent, filtered again, precipitated, washed, and lyophilized. After this purification process, the P4HB polymer was reported to have the following composition by elemental analysis: carbon 55.63%, hydrogen 7.41%, oxygen 37.28%, and nitrogen 41 ppm.

P4HB polymer has also been produced by the methods disclosed by EP 2534141 A1 to Van Walsem, and by WO 2013/023140 to Van Walsem.

Production of P4HB homopolymer from glucose has been reported by Zhou et al. Hyperproduction of poly(4-hydroxybutyrate) from glucose by recombinant *Escherichia coli, Microb. Cell Fact.* 11:54 (2012). The P4HB polymer was purified from the biomass.

Several other patents have disclosed methods to purify other PHA polymers from biomass, but none of these other PHA compositions or methods of purification are currently used to produce medical implants cleared or approved by the US Food and Drug Administration (FDA). U.S. Pat. No. 5,110,980 to Ramsay et al. discloses using hypochlorite solution to digest biomass in order to extract poly-3-hydroxyalkanoates. U.S. Pat. No. 5,942,597 to Noda et al. discloses solvent extraction of PHA polymers with melt temperatures of about 80° C. or higher from biomass. U.S. Pat. No. 6,043,063 to Kurdikar et al. discloses direct solvent extraction of certain PHA polymers from biomass with non-halogenated solvents. U.S. Pat. No. 6,087,471 to Kurdikar et al. discloses the use of pressure and high temperatures to solvent extract PHA polymers. U.S. Pat. No. 7,070,966 to Schumann et al. discloses methods to reduce the biomass and enzymatically decompose it. U.S. Pat. No. 7,098,298 to Kinoshita et al. discloses extracting PHA polymers with a monohydric alcohol having 4 to 10 carbon atoms. U.S. Pat. No. 7,118,897 to Narasimha et al. discloses the extraction of PHA polymers with solvents at high temperatures and under pressure, including the use of ethanol to extract PHA polymers. U.S. Pat. No. 7,226,765 to Narasimha et al. discloses the solvent extraction of PHA polymers at high temperatures. U.S. Pat. No. 7,252,980 to Walsem et al. discloses solvent extraction of PHA polymers, and recovery using centrifugation. U.S. Pat. No. 7,393,668 to Yanagita et al. discloses a method to extract PHA polymers from biomass by physical disruption in the presence of alkali followed by treatment of the separated PHA polymer with an enzyme and/or a surfactant to remove impurities adhering to the PHA polymer. U.S. Pat. No. 7,435,567 to Osakada et al. discloses methods to purify PHA polymers by digesting nucleic acids with hypochlorous acid. U.S. Pat. No. 7,576,173 to Walsem et al. discloses the extraction of PHA polymers with combinations of solvents. U.S. Pat. No. 8,357,508 to Mantelatto discloses a method to extract PHA polymers from biomass by injecting PHA solvents in liquid and vapor form into the biomass and heating.

The use of methanol to prewash *Pseudomonas putida* and *Ralstonia eutropha* 4-hydroxyvalerate-containing PHA polymer biomass prior to solvent extraction has been disclosed by Gorenflo et al. "Development of a process for the biotechnological production of 4-hydroxyvalerate-containing polyesters and characterization of their physical and mechanical properties", *Biomacromolecules* 2:45-57 (2001). The use of methanol to prewash *Pseudomonas putida* KT2440 biomass containing medium chain length PHA polymers has also been disclosed by Jiang et al. "Acetone extraction of mcl-PHA from *Pseudomonas putida* KT2440", *J. Microbiol. Meth.* 67:212-219 (2006). However, impurities with UV absorbances at 241 and 275 nm from the mcl-PHA polymer were still present following the use of methanol as a prewash step, and multiple additional steps were required to reduce their presence. The authors did not further identify these contaminants, but commented that nucleic acids and aromatic acids are known to absorb at these wavelengths. Moreover, methanol is highly toxic to humans in small quantities. In vivo, methanol is metabolized via formaldehyde to formic acid, which can cause permanent blindness by the destruction of the optic nerve. Ingestion, inhalation, or absorption of methanol can be fatal. For these reasons, the use of methanol in the preparation of implantable products should be avoided, and its use in pharmaceuticals is restricted and regulated by the FDA as a Class 2 solvent (International Conference on Harmonisation of Technical Requirements for Registration of Pharmaceuticals for Human Use (ICH) guidance for industry Q3C Impurities: Residual Solvents, 1997).

In the manufacture of implants using polymers, it is desirable that the polymeric materials have the lowest levels of impurities possible in order to prevent or minimize the reaction of the body to the impurities. Such undesirable reactions can include inflammation, cytotoxicity, irritation, pyrogenicity, genotoxicity, carcinogenicity, and acute, subchronic and chronic toxicity. Impurities may be placed in three broad categories, namely, organic impurities, inorganic impurities, and residual solvents. The purification of PHA polymers to a level where they are suitable for use in implants is particularly difficult due to their production in biological systems. Such production requires that the purification process remove a wide range of impurities, including, for example, lipids, proteins, peptides, heavy metals, endotoxin, polysaccharides, nucleic acids, amino acids, cell wall components, residual feed stocks, and residual media components if the PHA polymers are derived by fermentation. The latter can include yeast extract, soy peptone, antifoam agents, antibiotics, salts, amino acids, trace metals, sugars, and buffers. The purification is further complicated by the known affinity of PHA polymers for proteins, their relatively low solubility or lack of solubility in most solvents, and the difficulties of removing solvents from polymers to acceptable levels. And these difficulties must all be overcome while still yielding PHA polymers with good yields.

In order to improve the purity and biocompatibility of P4HB, it is desirable to identify new methods of purification that yield P4HB with reduced levels of: lipid, residues on ignition, nitrogen content, heavy metals, and residual solvent.

It is therefore an object of the present invention to provide compositions of P4HB with improved purity.

It is another object of the present invention to provide methods to produce P4HB with improved purity.

It is a further object of the present invention to provide implants made from P4HB compositions with improved purity.

It is still another object of the present invention to provide methods for human or animal use of P4HB implants with improved purity.

SUMMARY OF THE INVENTION

Compositions of P4HB with high purity have been developed. The compositions contain carbon, hydrogen or oxygen isotopes (e.g., $C^{12}$, $C^{13}$, $C^{14}$), oxygen (e.g., $O^{16}$, $O^{18}$), and/or hydrogen (e.g., deuterium, tritium) in their natural isotopic ratios, or are enriched for one or more isotopes of carbon, hydrogen or oxygen. The compositions are prepared by washing P4HB biomass prior to solvent extraction, then precipitating the P4HB from solution.

Methods have been developed that allow P4HB to be recovered from P4HB biomass with the following benefits: (i) higher purity, wherein the polymer contains less than 100 ppm of lipid assayed as palmitate and less than 40 ppm of nitrogen; (ii) a good yield of polymer with a recovery of greater than 75% of the polymer from the biomass; (iii) minimal loss of polymer molecular weight during recovery such that the polymer does not lose more than 10% of its weight average molecular weight during recovery; (iv) fewer recovery steps; (v) reduced solvent usage during extraction; (vi) easier drying of the polymer; (vii) lower cost; and (viii) faster overall process.

The highly pure P4HB compositions are suitable for preparing implants. The implants may be used for the repair of soft and hard tissues.

DETAILED DESCRIPTION OF THE INVENTION

I. Definitions

Figure 1A:
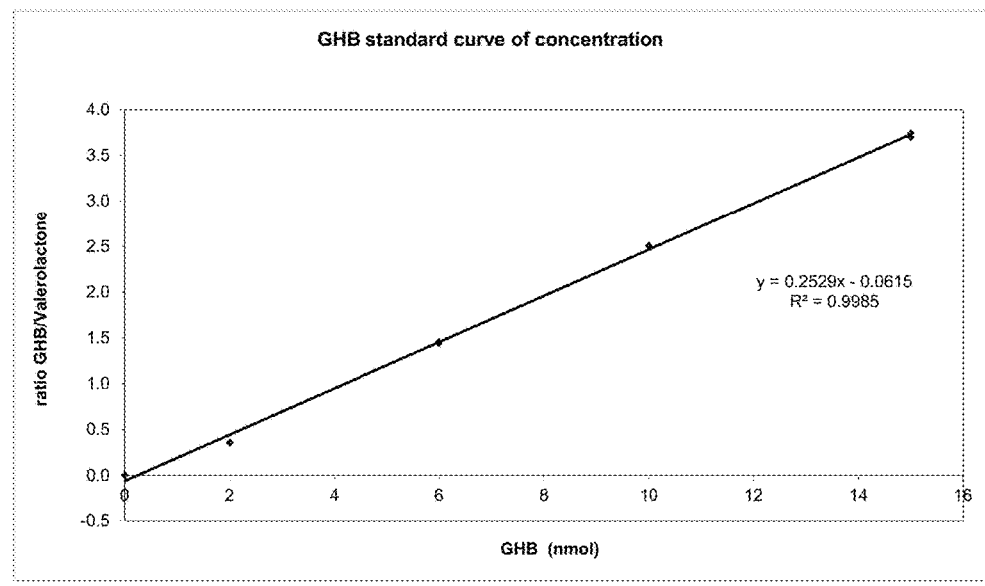
FIGS. 1A and 1B show standard curve for the GC-MS determination of serum 4HB (1A) and serum concentration of 4HB in test and control animals (1B).

"Poly-4-hydroxybutyrate" as generally used herein means a homopolymer of 4-hydroxybutyrate units. It may be referred to herein as P4HB. The P4HB can contain carbon, hydrogen and oxygen in their natural isotopic ratios, as well as polymers in which one or more isotopes are enriched.

"Copolymers of poly-4-hydroxybutyrate" as generally used herein means any polymer of 4-hydroxybutyrate with one or more different hydroxy acid units.

"Bioactive agent" is used herein to refer to therapeutic, prophylactic, and/or diagnostic agents. It includes without limitation physiologically or pharmacologically active substances that act locally or systemically in the body.

"Biocompatible" as generally used herein means the biological response to the material or device being appropriate for the device's intended application in vivo. Any metabolites of these materials should also be biocompatible.

"Blend" as generally used herein means a physical combination of different polymers or components, as opposed to a copolymer comprised of two or more different monomers.

"Carbon content" as used herein refers to the mass percentage of elemental carbon in a sample, and is determined by combustion analysis.

"Deuterated P4HB" referred to herein as D-P4HB.

"Endotoxin content" as used herein refers to the amount of endotoxin present in a sample, and is determined by the limulus amebocyte lysate (LAL) assay.

"Hydrogen content" as used herein refers to the mass percentage of elemental hydrogen in a sample, and is determined by combustion analysis.

"Heavy metal content" as used herein refers to the mass percentage of heavy metals in a sample, and is determined by the method of the United States Pharmacopeia (USP) <231>.

"Lipid content" as used herein refers to the concentration of lipids in the sample, and is determined by GC analysis after butanolysis, and is expressed in part per million (ppm) palmitic acid.

"Molecular weight" as used herein, unless otherwise specified, refers to the weight average molecular weight ($M_w$), not the number average molecular weight ($M_n$), and is measured by GPC relative to polystyrene.

"Nitrogen content" as used herein refers to the mass percentage of elemental nitrogen in a sample, and is determined by the Kjeldahl method of nitrogen analysis, and is expressed in parts per million (ppm).

"Residual solvent content" as used herein refers to the amount of solvent in a sample, and is determined by headspace GC-MS, and is expressed in ppm.

"Residue on ignition" as used herein refers to the amount of residual substance not volatized from a sample when it is ignited in the presence of sulfuric acid, and as determined by the method of the United States Pharmacopeia (USP)<281>.

"Resorbable" as generally used herein means the material is broken down in the body and eventually eliminated from the body. The terms "resorbable", "degradable", "erodible", and "absorbable" are used somewhat interchangeably in the literature in the field, with or without the prefix "bio". Herein, these terms will be used interchangeably to describe material broken down and gradually absorbed or eliminated by the body, whether degradation is due mainly to hydrolysis or mediated by metabolic processes.

"Sulfur content" as used herein refers to the mass percentage of elemental sulfur in a sample, is measured by inductively coupled plasma optical emission spectroscopy and is expressed in ppm.

II. Composition

Provided herein are compositions containing P4HB, recovered from a P4HB biomass. PHA4400 or TephaF-LEX® biomaterial is a homopolymer of 4-hydroxybutyrate manufactured by Tepha, Inc., Lexington, Mass.

The compositions can include known isotopes of carbon, hydrogen and oxygen in their natural isotopic ratios, or one or more isotopes which are enriched. The P4HB compositions have the following benefits: (i) higher purity; (ii) minimal loss of polymer molecular weight during recovery; and (iii) reduced residual solvent. There are no particular restrictions on the weight average molecular weight of the P4HB polymer. However, in a preferred embodiment, the weight average molecular weight of the P4HB polymer ranges from 20 kDa to 1,200 kDa, more preferably from 50 kDa to 800 kDa, and even more preferably from 200 kDa to 600 kDa.

The P4HB polymer is extracted after washing the P4HB biomass with a suitable solvent to remove impurities, for example, lipid and heavy metal impurities.

The structure for P4HB is shown above. The compositions disclosed herein include polymers in which known isotopes of hydrogen, carbon and/or oxygen are enriched. Hydrogen has three naturally occurring isotopes, which include $^1H$ (protium), $^2H$ (deuterium) and $^3H$ (tritium), the most common of which is the $^1H$ isotope. The isotopic content of the polymer can be enriched for example, so that the polymer contains a higher than natural ratio of a specific polymer. The carbon and oxygen content of the homopolymer or copolymer can be also be enriched to contain higher than natural ratios of isotopes of carbon, and oxygen, including, but not limited to $^{13}C$, $^{14}C$, $^{17}O$ or $^{18}O$. Other isotopes of carbon, hydrogen and oxygen are known to one of ordinary skill in the art.

A preferred hydrogen isotope enriched in P4HB is deuterium, deuterated P4HB. The percent deuteration on can be up to at least 1% and up to 5, 10, 15, 20, 25, 30, 35, 40, 45, 50, 55, 60, 65, 70, 75, 80, or 85% or greater.

A. P4HB Biomass

There is no particular restriction on the microorganism that can be used provided it is a microorganism that is capable of producing and storing P4HB in its cells. In a preferred embodiment, the P4HB biomass is concentrated by centrifugation prior to purification, and refrigerated or frozen. It is not necessary to completely dry the P4HB biomass, however, in a particularly preferred embodiment, the P4HB biomass is dried to a low moisture content of less than 5% residual water, or more preferably less than 2% residual water. Suitable methods for drying the biomass include, but are not limited to, spray drying, vacuum drying, lyophilization, or spray granulation.

Examples of suitable microorganisms that can be used as sources of P4HB biomass, including mutated microorganisms and microorganisms genetically modified to produce P4HB, include microorganisms belonging to the genus *Escherichia, Aeromonas, Alcaligenes, Azotobacter, Bacillus, Clostridium, Halobacterium, Nocardia, Nocardia, Actinomyces, Aguaspirillum, Paracoccus, Rhodospirillum, Pseudomonas, Ralstonia, Zoogloea Candida, Saccharomyces,* and *Yarrowia*. Particularly preferred microorganisms for the production of P4HB biomass include *E. coli* strain MBX1177, a derivative of strain DH5α selected for its ability to grow with 4-hydroxybutyric acid as the sole carbon source, transformed with pFS30, a plasmid containing the genes encoding PHA synthase from *Ralstonia eutropha*, 4-hydroxybutyryl-CoA transferase from *Clostridium kluyveri*, and β-lactamase, as disclosed by WO 99/32536 to Martin and WO 00/56376 to Williams. Other microorganisms that may be used to produce P4HB biomass include the mutant strain SK2813 derived from *A. eutrophus* JMP222 as disclosed by German Patent No. DE 3937649A1 to Steinbüchel et al., and the mutant strain of *E. coli* JM109 deficient in native succinate semialdehyde dehydrogenase genes and harboring genes for succinate degradation from *Clostridium kluyveri* and PHB synthase from *Ralstonia eutropha*, together with genes for expression of four PHA binding proteins, as disclosed by Zhou et al. Hyperproduction of poly(4-hydroxybutyrate) from glucose by recombinant *Escherichia coli, Microb. Cell Fact.* 11:54 (2012).

Suitable P4HB producing microorganisms may be cultured by methods known in the art, and reported as described above (for example by WO 99/32536 to Martin, WO 00/56376 to Williams, EP 2534141 A1 to Van Walsem, WO 2013/023140 to Van Walsem, and references therein), without any particular restrictions. Preferably, the microorganism and the culturing conditions are selected to yield high P4HB contents. In a particularly preferred embodiment, the microorganisms contain at least 50 wt % P4HB measured as a percentage of dry cell weight.

4-hydroxybutyrate polymers enriched for specific isotopes of hydrogen, oxygen or carbon can be made using the same fermentation method used to make PHA4400, however, using substrates that include the isotope of choice. For example, deuterated 1,4-butanediol [HO(CD$_2$)$_4$OH or 1,4-butanediol,1,1,2,2,3,3,4,4-d$_8$] can be used as a feed instead of 1,4-butanediol. During the fermentation process, the deuterated 1,4-butanediol is converted into deuterated 4HB (i.e. [$^2$H$_6$]-4HB) and polymerized into D-P4HB. The labeled polymer can be isolated and purified by the same process used for PHA4400.

B. Washing Solutions Solvents

The P4HB biomass is preferably suspended in ethanol, and washed at ambient temperature for one hour. The ratio of ethanol to P4HB biomass is preferably about 4 Kg of ethanol per Kg of P4HB biomass. The optimum amount of ethanol required to wash the biomass will be dependent upon the P4HB biomass, the feedstock used to prepare the biomass, washing time and temperature, moisture content of the biomass, and the amount of lipid and other impurities to be removed in the washing step. Aqueous solutions of ethanol may also be used to wash the biomass although washing with absolute ethanol is the preferred method. Alternatively, 95% ethanol (190 proof ethanol) or other aqueous concentrations of ethanol may be used.

III. Methods of Extracting Higher Purity P4HB

Methods have been developed that allow P4HB to be recovered from P4HB biomass with the following benefits: (i) higher purity; (ii) a good yield of polymer; (iii) minimal loss of polymer molecular weight during recovery; (iv) fewer recovery steps; (v) reduced solvent usage during extraction; (vi) easier drying of the polymer; (vii) lower cost; and (viii) faster overall process.

A. Washing of P4HB Biomass

It has been discovered that washing the P4HB biomass with ethanol prior to extraction of the P4HB polymer results in the removal of lipids and other impurities that can otherwise contaminate the extracted P4HB polymer. Since ethanol is a poor solvent (i.e. non-solvent) for P4HB, but a good solvent for lipids, washing removes lipids but does not dissolve P4HB. It has also been discovered, that the P4HB biomass can be washed with ethanol without causing any transesterification of the P4HB polymer, and therefore the washing step may be done without any significant loss of polymer molecular weight. Furthermore, it has been discovered that washing the P4HB polymer with ethanol prior to extraction removes impurities that can cause a discoloration, or yellowing, of the purified product. Together, these improvements allow P4HB to be purified without multiple precipitation steps that are commonly reported for the extraction of PHA polymers.

A major advantage of using ethanol to wash the P4HB biomass is its classification as a Class 3 solvent (International Conference on Harmonisation of Technical Requirements for Registration of Pharmaceuticals for Human Use (ICH) guidance for industry Q3C Impurities: Residual Solvents, 1997). Class 3 solvents are those solvents that are considered to have low toxic potential to man, and have no set health based exposure limit.

In a preferred embodiment, the P4HB biomass is suspended in ethanol, and washed at ambient temperature for one hour. The ratio of ethanol to P4HB biomass is preferably about 4 Kg of ethanol per Kg of P4HB biomass. The optimum amount of ethanol required to wash the biomass will be dependent upon the P4HB biomass, the feedstock used to prepare the biomass, washing time and temperature, moisture content of the biomass, and the amount of lipid and other impurities to be removed in the washing step. Aqueous solutions of ethanol may also be used to wash the biomass although washing with absolute ethanol is the preferred method. Alternatively, 95% ethanol (190 proof ethanol) or other aqueous concentrations of ethanol may be used.

In a particularly preferred embodiment, P4HB biomass derived from recombinant *E. coli* K12 is washed with ethanol to remove impurities. The use of ethanol to extract impurities from the *E. coli* K12 P4HB biomass has been found to be very efficient. During the washing step, the ethanol will typically become discolored with a yellow appearance as impurities are extracted into the ethanol. These impurities have been identified as mostly saturated and unsaturated fatty acids by GC analysis, with C16:0 and C18:1 fatty acids and oleate most prevalent. At the end of the washing step, the concentrated ethanol extract (which has the appearance of a black tar) has a high nitrogen content that will typically be around 0.65 wt %. As such, the ethanol wash has been shown to remove nitrogen containing contaminants as well as lipids and colored contaminants.

After washing with ethanol, the biomass may be separated from the ethanol wash by a method of solid-liquid separation, and collected by any suitable means. In a preferred embodiment, the P4HB biomass is collected by filtration or centrifugation. If desired, additional washing of the collected P4HB biomass may be performed, or the P4HB biomass may be rinsed with ethanol or aqueous ethanol during collection. Although it is not necessary to completely dry the P4HB biomass after removing the ethanol wash, in a preferred embodiment, the ethanol washed P4HB biomass is air-dried. In a particularly preferred embodiment, the P4HB biomass is dried to a residual ethanol concentration of between 1 and 30 wt % ethanol. It has been discovered that the presence of higher quantities of residual ethanol in the washed P4HB biomass does not adversely impact the polymer recovery yield or the weight average molecular weight of the product.

In comparison to aqueous based extraction procedures, it has been discovered that washing the biomass with ethanol yields a P4HB biomass that is easier to dry. When a dry P4HB biomass is required, washing with ethanol not only removes impurities, it also displaces water from the biomass, which significantly facilitates drying. As a result washing with ethanol can save on the costs of drying, and speed up and simplify the recovery process.

B. Extraction of P4HB Biomass

After the P4HB biomass has been washed with ethanol, the P4HB polymer can be extracted with a solvent. Ideally, the P4HB polymer has a high solubility in solvents used to extract the polymer. Preferred solvents for extracting the P4HB polymer from the ethanol washed biomass include methylene chloride, chloroform, dichloroethane, tetrachloroethane, trichloroethane, dibromomethane, bromoform, tetrahydrofuran, acetone, dimethylformamide, and 1,4-dioxane. The ratio of solvent to biomass depends upon the polymer content of the biomass, and on the nature of the solvent. If too little solvent is used the viscosity of the extracted polymer solution can become too high making further processing of the polymer solution difficult. In a particularly preferred embodiment, the amount of solvent needed is set so that a polymer solvent solution containing 2-5 wt % P4HB polymer is formed by the end of the extraction.

It has been discovered that the amount of solvent required to extract the P4HB polymer with a good yield is significantly reduced when ethanol is used to wash the biomass prior to extraction of the polymer. In addition to saving the cost of additional solvent, the reduced extraction volume also decreases the amount of non-solvent for the P4HB polymer that is subsequently needed to precipitate the polymer from the solvent solution. Although it is preferred to precipitate the polymer from solution to provide a polymer with the highest possible purity, reduced costs of solvent evaporation are realized if the polymer is simply concentrated after extraction and not precipitated.

C. Precipitation of P4HB Polymer and Drying

The P4HB polymer may be collected from solvent solutions of P4HB, which have been extracted from P4HB ethanol washed biomass, by precipitating the polymer with a non-solvent. This is preferable to crystallizing the polymer from a solvent solution, which can require very large amounts of solvent in order to yield highly pure product and can consequently be very expensive.

The non-solvent used to precipitate the P4HB polymer from a solvent solution of P4HB is preferably an alcohol or aqueous alcohol that is a poor solvent for the P4HB polymer. Water, ethanol, aqueous ethanol, and methanol may be used to precipitate the P4HB, however, methanol is not a preferred non-solvent because of the potential toxicity of residues of methanol in the purified product. In a particularly preferred embodiment, the same type of solvent (or an aqueous solution of the solvent) that is used to wash the P4HB biomass is also used as the non-solvent to precipitate the P4HB polymer from the P4HB polymer solution. This is particularly desirable since it limits the number of solvents being used in the extraction process, and therefore limits the number of solvent residues that need to be removed and assayed in the final purified product. In a particularly preferred embodiment, ethanol is used to wash the P4HB biomass, and either ethanol or aqueous ethanol is used as a non-solvent to precipitate the polymer from a P4HB solvent solution. In an even more preferred embodiment, the P4HB biomass is washed with ethanol, and the polymer is precipitated from a solvent solution of P4HB with aqueous solutions of ethanol containing 30-80% by weight of ethanol. The P4HB may be washed after precipitation with ethanol or an aqueous solution of ethanol.

The ratio of non-solvent to the P4HB solvent solution that is required to precipitate the P4HB polymer will depend on the non-solvent, the solvent for the P4HB, the temperature, the molecular weight of the P4HB, and the desired recovery yield. In a typical procedure, the ratio of P4HB non-solvent to P4HB solvent ranges from 1:2 to 4:1, and is more preferably closer to 1:1.

There are no particular limitations on the temperature that should be used to precipitate the P4HB polymer from the solvent solution, however, the temperature should be lower than the boiling point of the solvent solution and higher than its freezing temperature. In a preferred embodiment, the temperature of the precipitation step should be less than 50° C. and greater than 0° C., and more preferably at a temperature of less than 25° C.

The precipitated P4HB polymer may be collected by any suitable means for separating solids and liquids including the use of filtration and centrifugation. The collected P4HB polymer may be further washed with a non-solvent for P4HB. In a preferred embodiment, the collected P4HB polymer may be washed with ethanol or aqueous ethanol. Further washing with ethanol may also be used to displace water from the collected polymer in order to make it easier to dry the P4HB polymer.

A major advantage of the method disclosed herein is that a highly pure P4HB polymer can be obtained with a single precipitation step. Additional precipitation steps may be performed by re-dissolving the P4HB polymer in a solvent, and repeating the precipitation procedure. However, in the preferred embodiment the P4HB polymer is purified with just a single precipitation step, which eliminates the requirement to use large quantities of solvent for the P4HB purification.

After collecting the precipitated polymer, the P4HB may be desolventized and dried by any suitable means. Suitable methods to remove residual solvent and dry the polymer include air-drying and drying under vacuum. Desiccants may also be used to dry the polymer, and elevated temperatures can be used to shorten the time required to remove residual solvent and dry the polymer.

D. Comparison of Purification Methods

In the procedures previously disclosed by WO 99/32536 to Martin and WO 00/56376 to Williams, a five step process was used to purify P4HB. The steps include: (a) a step to fluidize and lyophilize the P4HB biomass, (b) a step to extract the P4HB polymer with tetrahydrofuran (THF) at 60° C., and filter insoluble matter, (c) a step to precipitate the P4HB polymer into water, (d) a step to redissolve the P4HB polymer in solvent and filter it again to remove insoluble matter, and (e) a step to precipitate the polymer, wash the polymer, and lyophilize the polymer. This process yields a P4HB polymer with the following specification: (i) carbon content of 55.63%; (ii) hydrogen content of 7.41%; and nitrogen content of 41 ppm. The lipid content of the P4HB polymer is not disclosed in WO 99/32536 to Martin and WO 00/56376 to Williams, however, for comparison purposes it was determined as described in Example 5 and found to be approximately 900 ppm palmitate fatty acid (see Example 6).

In contrast, the new methods developed and disclosed herein, allow the P4HB polymer to be purified in essentially three steps: (a) a step to wash the P4HB containing biomass with ethanol, (b) a step to solvent extract the P4HB biomass and filter insoluble matter, and (c) a step to precipitate the P4HB polymer from the solvent with a non-solvent system of aqueous alcohol, wash the P4HB polymer with ethanol or aqueous ethanol, and desolventize and dry the P4HB polymer. Not only does the new process have significantly fewer steps, it also yields P4HB polymer of higher purity. The Table below shows a side-by-side comparison of the P4HB extraction steps disclosed in WO 99/32536 and the extraction method described in this application

| WO 99/32536 | Disclosed method |
|---|---|
| fluidize and lyophilize | Wash Biomass with ethanol |
| Extract PHA with THF | Solvent extract P4HB and filter insoluble matter |
| Precipitate P4HB into water | — |
| Redissolve P4HB in THF and remove impurities | — |
| Precipitate P4HB into solvent, wash and lyophilize polymer | Precipitate P4HB from solvent into non-solvent, wash, desolventize and dry |

In a preferred embodiment, the purity of the P4HB polymer purified according to the methods described in sections IIA, IIB and IIC meets the following specification: (i) carbon content of 55.81%±0.5%; (ii) hydrogen content of 7.02%±0.3%; (iii) lipid content of <100 ppm (measured as palmitate); (iv) residual solvent content <5 ppm; (v) 4-hydroxybutyrate content of 99.7%±2% by weight; (vi) residue on ignition of <0.2%; (vii) a heavy metal content of <20 ppm; and a sulfur content of <50 ppm. As shown in Example 2, the new process also yields a P4HB polymer with a nitrogen content of less than 40 ppm.

IV. Methods of Manufacturing Implants with High Purity P4HB

Implants made using high purity P4HB polymer have substantially improved properties for many medical applications. In particular, these implants have low levels of organic impurities, inorganic impurities, and residual solvents that can react with the body upon implantation. The low levels of these impurities will reduce or minimize undesirable reactions such as inflammation, cytotoxicity, irritation, pyrogenicity, subchronic and chronic toxicity. Devices made from or including high purity P4HB may be prepared with endotoxin contents of less than 20 endotoxin units per device.

Implants made from or including high purity P4HB polymer, and blends containing P4HB, may be used for soft and hard tissue repair, regeneration, and replacement. These implants may be used in medical devices, including but not limited to: suture, barbed suture, braided suture, monofilament suture, hybrid suture of monofilament and multifilament fibers, braids, ligatures, knitted or woven meshes, knitted tubes, catheters, monofilament meshes, multifilament meshes, patches, wound healing device, bandage, wound dressing, burn dressing, ulcer dressing, skin substitute, hemostat, tracheal reconstruction device, organ salvage device, dural substitute, dural patch, nerve guide, nerve regeneration or repair device, hernia repair device, hernia mesh, hernia plug, device for temporary wound or tissue support, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of vesicoureteral reflux, bladder repair device, sphincter muscle repair device, injectable particles, injectable microspheres, bulking or filling device, bone marrow scaffold, clip, clamp, screw, pin, nail, medullary cavity nail, bone plate, interference screw, tack, fastener, rivet, staple, fixation device for an implant, bone graft substitute, bone void filler, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, device for treatment of osteoarthritis, viscosupplement, stent, including coronary, cardiovascular, peripheral, ureteric, urethral, urology, gastroenterology, nasal, ocular, or neurology stents and stent coatings, stent graft, cardiovascular patch, catheter balloon, vascular closure device, intracardiac septal defect repair device, including, but not limited to, atrial septal defect repair devices and PFO (patent foramen ovale) closure devices, left atrial appendage (LAA) closure device, pericardial patch, vein valve, heart valve, vascular graft, myocardial regeneration device, periodontal mesh, guided tissue regeneration membrane for periodontal tissue, ocular cell implant, imaging device, cochlear implant, embolization device, anastomosis device, cell seeded device, cell encapsulation device, controlled release device, drug delivery device, plastic surgery device, breast lift device, mastopexy device, breast reconstruction device, breast augmentation device (including devices for use with breast implants), breast reduction device (including devices for removal, reshaping and reorienting breast tissue), devices for breast reconstruction following mastectomy with or without breast implants, facial reconstructive device, forehead lift device, brow lift device, eyelid lift device, face lift device, rhytidectomy device, thread lift device (to lift and support sagging areas of the face, brow and neck), rhinoplasty device, device for malar augmentation, otoplasty device, neck lift device, mentoplasty device, cosmetic repair device, and device for facial scar revision.

The devices may include a therapeutic, prophylactic, or diagnostic agent. These include, for example, compounds for the treatment, prevention, diagnosis, cure, or mitigation of one or more symptoms of a disease or disorder, substances that affect the structure or function of the body, or pro-drugs, which become biologically active or more active after they have been placed in a predetermined physiological environment. These include biologically, physiologically, or pharmacologically active substances that act locally or systemically in the human or animal body. Examples can include, but are not limited to, small-molecule drugs, proteins, peptides, sugars and polysaccharides, nucleic acids, lipids, and combinations thereof, which may function as anti-inflammatory agents, immunomodulatory agents, molecules that affect cell migration, molecules that affect cell division, molecules that affect cell proliferation and differentiation, molecules that stimulate phenotypic modification of cells, molecules that affect angiogenesis, molecules that affect vascularization, molecules that affect extracellular matrix disposition, signaling ligands, antibodies, growth factors, integrins, antibiotics, steroids, hydroxyapatite, silver particles, vitamins, and non-steroidal anti-inflammatory drugs. Materials may also include extracellular matrix materials like fibronectin, laminin, vitronectin, chitosan and derivatives thereof, alginate and derivatives thereof, collagen, and hyaluronic acid and derivatives thereof. Nucleic acids include antisense molecules, aptamers, siRNA, nucleic acids, and combinations thereof.

The present invention will be further understood by referenced to the following non-limiting examples.

Example 1: Washing of P4HB Biomass with Ethanol

A biomass containing P4HB ($M_w$ of 468 kDa, by Gel Permeation Chromatography (GPC) relative to standards of polystyrene), prepared according to Example 1 of WO 99/32536 to Martin, was suspended in ethanol at room temperature. After one hour, the P4HB biomass was removed by filtration, and the ethanol wash concentrated to yield a black tar. Analysis of the tar by NMR demonstrated that the ethanol extract of the P4HB biomass was composed almost entirely of saturated and unsaturated lipids.

The nitrogen content of the tar was also determined to be 0.65 wt %.

Example 2: Purification of Ethanol Washed P4HB Biomass

The ethanol washed P4HB biomass derived from Example 1 was centrifuged in a basket centrifuge to remove the bulk of the ethanol washing solution. The P4HB polymer was extracted into an organic solvent, precipitated into aqueous ethanol (30%), and collected for analysis. The nitrogen content of the P4HB polymer extracted from the ethanol washed P4HB biomass was found to be 37 ppm as determined by the Kjeldahl method (Bradstreet, Anal. Chem., 26(1):185-187 (1954). The carbon and hydrogen mass fractions of the purified P4HB polymer were determined by elemental combustion analysis using a LECO CHN 2000 instrument (following the manufacturer's instructions), and were found to be 55.89% and 7.05%, respectively. These values are close to the theoretical values for poly-4-hydroxybutyrate: carbon 55.81%, and hydrogen 7.02%. No significant loss of molecular weight of the P4HB polymer was observed. The weight average molecular weight of the purified P4HB polymer was determined by GPC relative to polystyrene, and was found to be 449 kDa (versus 468 kDa prior to purification) indicating that the ethanol washing step did not cause molecular weight loss by transesterification of P4HB with ethanol. The purity of the P4HB polymer was determined by GC (gas Chromatography) analysis (as described in Example 3), and was found to be 99.5%. Proton NMR analysis of the purified P4HB polymer demonstrated that the polymer was of high purity with little evidence of contaminating lipids at 1.2 ppm in the NMR spectrum. The endotoxin content of the purified P4HB polymer was 0.22 endotoxin units (EU)/g which is low enough to allow the manufacture of implants using P4HB with an endotoxin content of less than 20 endotoxin units per device.

Example 3: Analysis of P4HB Purity by GC

The purity of a P4HB polymer in an unknown sample may be measured by gas chromatography after derivatization of the polymer using a butanolysis reaction to form volatile esters. The butanolysis reaction is an acid-catalyzed transesterification reaction with 1-butanol that converts the P4HB polymer into two major derivatives, butyl-4-hydroxybutyrate and butyl-4-chlorobutyrate. The latter yields a sharp peak in the GC chromatograph that can easily be integrated, and its peak is proportional to the amount of P4HB in the sample.

The reagent for the butanolysis reaction is prepared by mixing equal parts (v/v) of 1-butanol and 4M hydrochloric acid (HCl) in 1,4-dioxanone to yield a solution of 2M HCl in butanol/dioxane. An internal standard, such as diphenylmethane, may be added to the solution at a concentration of 2.0 mg/ml to normalize injection volumes.

The butanolysis reaction is performed by adding 3 mL of the butanolysis reagent (prepared as described above) to a known mass of a P4HB sample (approximately 25 mg) in a vial. The vial is sealed, and heated at 90-92° C. for 16-20 hours. (A standard curve may be generated by butanolysis of known quantities of high purity gamma-butyrolactone (GBL)) After heating, the vials are allowed to cool, 3 mL of water are added, and the contents of the vial are thoroughly mixed, and then allowed to separate. The 4HB content in the sample may then be determined by GC analysis of the separated organic layer in the vial, using the GBL standard samples to create a standard curve.

The GC analysis is performed by injecting 1 µL of the organic phase containing the volatile butyl esters into a suitable gas chromatograph. One suitable GC set up comprises an Agilent 6890 GC (Agilent Technologies, CA, USA) equipped with an autosampler, a flame ionization detector, and a SPB-35 capillary column from Supelco, Inc. (PA, USA) (30 m×0.25 mm×0.25 microns) with helium used as a carrier gas at 2 ml/min. The inlet temperature is set at 225° C., and the split ratio is 50:1. The oven temperature program is set at 80° C. for 2 min, increasing 10° C. per minute to 280° C., and holding at 280° C. for 2 minutes. At the detector, the temperature is set at 290° C., the hydrogen flow rate is 40 ml/min, the helium makeup gas is set at 45 ml/min and the detector air flow rate is set at 450 ml/min.

The mass of 4HB in the P4HB polymer is determined from integration of the sharp peak of butyl-4-chlorobutyrate in the GC chromatograph. The mass of 4HB in the sample can be determined from the GBL standard curve (plotted as mass vs. the integral area of the butyl-4-chlorobutyrate peak. The purity of the sample is determined as the mass percentage of 4HB relative to the mass of polymer times 100%. The purity of P4HB purified by methods described herein is 99.7+/−2 wt %.

Example 4: Additional Example of Purification of P4HB from P4HB Biomass

A P4HB biomass prepared according to Example 1 of WO 99/32536 to Martin et al. can be pre-washed with ethanol to remove colored contaminants and fatty acids prior to solvent extraction of the polymer using the following procedure.

The dried P4HB biomass is suspended in absolute ethanol at a ratio of 1 Kg of biomass to 4 Kg of ethanol, and stirred aggressively for one hour at room temperature. The resulting biomass slurry is transferred to a basket centrifuge, and the slurry is centrifuged to remove the wash solvent. During centrifugation, an additional wash with ethanol is performed to further displace the wash solvent. Centrifugation is performed to reduce the residual solvent content of the biomass to less than 15% by weight. After washing, the biomass is removed from the centrifuge, analyzed for residual volatiles and collected for polymer extraction.

The collected washed biomass is transferred to an extraction vessel and extracted into a suitable solvent at an elevated temperature for 4 hours. Suitable extraction solvents include polar organic solvents such as chloroform, dichloromethane, dimethylformamide, tetrahydrofuran, acetone, dioxane, and mixtures of these. After extraction is completed, the extract is filtered to remove cell debris and insolubles, and the polymer is precipitated by pumping the filtrate into a non-solvent for P4HB. A solution of ethanol and water (between 30-80% ethanol by wt) is used as the non-solvent. When the filtrate is pumped into this aqueous ethanol solution, the P4HB precipitates as a solid, and is collected and further washed with ethanol. After washing, the collected P4HB polymer is transferred to a vacuum drying oven and dried at 45° C. under vacuum.

Example 5: Analysis of Fatty Acid (Lipid) Content of P4HB by GC

The analysis for fatty acids in a sample of P4HB is carried out in a similar manner to the GC butanolysis purity analysis per Example 3, except that a fatty acid is used as a quantitative standard, rather than GBL. The fatty acid palmitate, or its methyl ester, is a suitable standard. The butanolysis reaction converts fatty acids, or fatty acid esters, into the corresponding fatty acid butyl esters. These volatile esters are analyzed by injection onto a GC as in Example 3. Palmitic acid, the most prevalent lipid in animals, plants and microorganisms, is used as a representative lipid or fatty acid to evaluate the purity and lipid content of a sample, even though other fatty acids or lipids may also be present in the sample. A standard curve for peak area of butyl palmitate vs. its mass is generated and used to determine the fatty acid content of the P4HB sample. Fatty acid concentration is reported as ppm palmitate fatty acid.

Example 6: Determination of the Lipid Level in the P4HB Polymer Purified According to Example 1 of WO 99/32536 to Martin Seven polymer samples of P4HB purified according to Example 1 of WO 99/32536 to Martin were analyzed in triplicate for lipid content as in Example 5. The amount of lipid in the samples was found to range from 304 to 2,207 ppm and the average was found to be 873 ppm, with a standard deviation of 629 ppm.

In comparison, the residual lipid content found in samples of P4HB purified per the method of Example 2 was found to be less than 100 ppm.

Example 7: Determination of Heavy Metal Content, Residue on Ignition, Residual Solvent, and Sulfur Content in High Purity P4HB Polymer P4HB polymer purified according to the method described herein was analyzed for heavy metal content, residue on ignition, the presence of residual solvent, and sulfur content. The heavy metal content of the polymer was determined by USP <231> (a colorimetric procedure based on the precipitation of insoluble metal sulfides) and was found to be <20 ppm. The residue on ignition of the purified polymer was determined by USP <281> and was found to be <0.1%. The amount of residual solvent in the polymer was measured by Headspace GC-MS using an HP 5890 II GC equipped with a 5972 MS Detector and a ZB-5 Capillary Column (60 m×0.32 mm ID×1 µm FT). Samples of polymer were heated in capped vials at 130° C. for one hour before analysis. The residual solvent content of the P4HB polymer was found to be <5 ppm. The sulfur content of the purified P4HB polymer was determined by inductively coupled plasma optical emission spectroscopy, and found to be <50 ppm.

Example 8: Preparation of Deuterated P4HB (D-P4HB) Implants and Implantation Procedure Experiments were conducted to quantify the release of 4-hydroxybutyric acid (4HB) during the degradation and absorption of a PHA4400 (TephaFLEX) implant. During this study, the blood concentration of deuterium labeled 4HB (D-4HB) was monitored in rabbits that had been implanted with deuterium labeled PHA4400 (D-PHA4400). The blood concentration of the native (i.e. unlabeled) 4HB was also monitored to determine if the D-4HB released from a D-PHA4400 implant affected the native levels of 4HB. Additionally, the rabbits' blood was analyzed for traditional clinical blood parameters.

A PHA4400 implant will degrade in the body primarily by hydrolysis to produce 4HB. This monomer is a normal constituent of the mammalian blood serum and is found within a variety of tissues, including brain, heart, kidney, liver, lung, muscle and brown fat (Nelson, et al., *J. Neurochem.*, 37:1345-1348 (1981)). The concentration of 4HB in these tissues ranges from 2.3 to 37.4 nmoles/g of tissue (or 0.24 to 3.8 milligrams per Kg of tissue, based on a formula weight of 104 g/mol). The body quickly metabolizes 4HB, and its half-life is approximately 27 minutes (Nelson, et al., *J. Neurochem.*, 37:1345-1348 (1981); Sendelbeck, et al., *Drug Metab. dispos.* 13:291 (1985)). 4HB is eliminated from the body primarily by metabolism (via the Krebs Cycle) and secondarily by beta-oxidation ultimately to carbon dioxide and water.

D-P4HB was made using the same fermentation method disclosed herein. However, deuterated 1,4-butanediol [HO(CD$_2$)$_4$OH or 1,4-butanediol,1,1,2,2,3,3,4,4-d$_8$] was used as a feed instead of 1,4-butanediol. During the fermentation process, the deuterated 1,4-butanediol was converted into deuterated 4HB (i.e. [$^2$H$_6$]-4HB) and polymerized into D-P4HB. The labeled polymer was isolated and purified by the same process used for P4HB. NMR spectra for the D-P4HB (Lot No. DM21.87) showed that the $^{13}$C NMR spectrum of the labeled polymer is a bit more complicated than the unlabeled polymer since each carbon attached to deuterium is split into a multiplet. The carbonyl (no bound D) appears as a singlet. The $^1$H NMR spectrum of the labeled polymer does not show the deuterium, but rather shows residual protons at their expected chemical shifts.

Elemental analysis of the polymer showed the level of carbon to be 52.08%, which is within the acceptable limits of the expected value of 52.20% (±0.5%) for the repeating formula of C$_4$D$_6$O$_2$ calculated for heavy isotope. The weight percentage of deuterium was not calculated. The polymer was put through an additional round of purification to yield a new lot (Lot No. 225-030). The Mw of this new lot was determined to be 525 K. GC analysis for lot no. 225-030 passed the purity assay (98.3% purity).

Implantation Method

Eight rabbits were used for the study. Six (6) disks of D-PHA4400 material (M6) were implanted subcutaneously in the back of each of six rabbits, so each animal was implanted with approximately 341 mg of D-PHA4400. The other two rabbits were implanted with 6 disks of high density polyethylene (HDPE) as controls. To facilitate later recovery of the implants, the peri-incision areas were tattooed.

Following surgery, one rabbit in the study (rabbit 8) was found to have a hard mass on the abdomen a few days after implantation. Treatment with antibiotics was unsuccessful and the animal was euthanized at day 28. Due to its location in the abdominal muscle, this mass was most likely not implant related, but is believed to have pre-dated the implants. To replace this animal, an additional animal (rabbit 9) was added to the study at 1 month. The recovery of the other animals (1-7, 9) in the study was uneventful.

The rabbits were maintained for a period of 1 year and blood was drawn from each rabbit monthly for analysis of

[$^2$H$_6$]-4HB and 4HB concentrations in the serum. Blood samples were collected using fluoride anticoagulation, centrifuged and the serum samples is stored frozen at −20° C. for batch analysis at 3 and 6 months and 1 year. Clinical blood chemistry parameters were determined at pre-implant, 3 months, 6 months and 1 year (Note: Additional clinical testing was done at 4 and 5 months). At the conclusion of the study, the animals were sacrificed and any residual implant material harvested for analysis of mass loss and Mw. Tissue samples taken from the implantation sites of each animal were processed for histological analysis.

Blood Analysis Methodology

To analyze for the presence of 4HB in the blood, serum samples (0.5 ml) were spiked with 8.6 nmol of 5-hydroxypentanoate (i.e. valerolactone) as an internal standard, deproteinized with sulfosalicylic acid, centrifuged and extracted with ether (3 times). Pooled extracts were dried over sodium sulfate, concentrated and hydrolyzed with NaOH (1 ml, 10 mM). After evaporation, the residue was converted to the trimethyl silyl derivative. Capillary gas chromatography-mass spectrometry (GC-MS) analysis was performed using a Hewlett-Packard MS-engine in the ammonia positive chemical ionization mode. Ions were monitored for unlabeled 4HB at m/z 249, [$^2$H$_6$] 4HB at m/z 255 and the valerolactone internal standard at m/z 263, as the trimethyl silyl derivatives. A reference standard of [$^2$H$_6$] 4HB was prepared by hydrolysis of the D-PHA4400. The conditions of the assay were optimized by preparation of standard curves using spare samples of rabbit plasma. The temperature profile of the GC column was optimized so that the 3 compounds elute free of interferences from unknown compounds and this was verified by the identity of the mass isotopomer distributions of the 3 compounds in pure aqueous solutions and in plasma extracts. The standard curve was linear in the range of 0 to 15 nmol and is shown in FIG. 1A.

Results

Figure 1B:
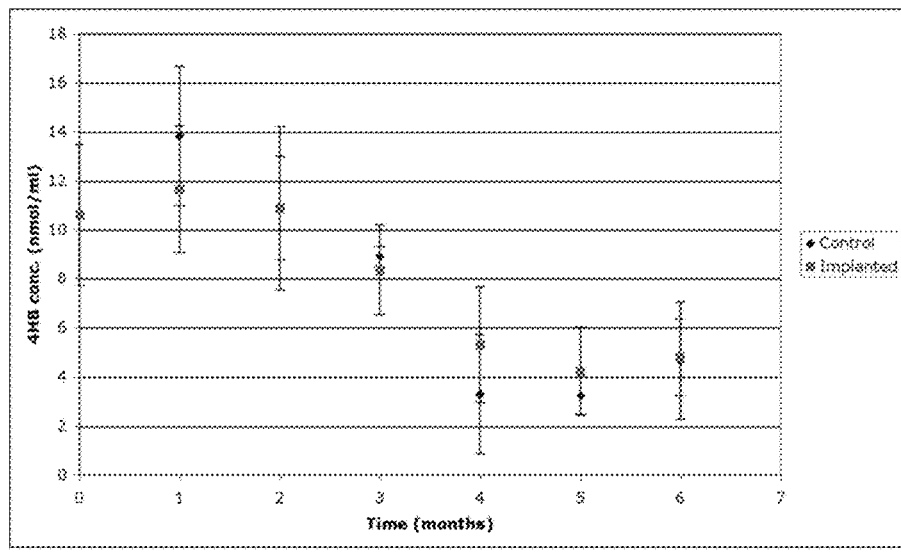

Serum samples were analyzed through 6 months of the study. The average basal serum concentration of 4HB (i.e. prior to implantation of the D-PHA4400 and control disks) was found to be 10.6±2.9 nmol/ml. During the 6-month observation period, there was no significant difference in the serum concentration of 4HB between the control and the D-PHA4400 implanted animals. Over the 6-month observation period, the serum concentration of 4HB decreased to approximately 4 nmol/ml in both the control and the D-PHA4400 implanted animals, as shown in FIG. 1B and Table 1.

TABLE 1

Blood concentration of 4HB following implant of deuterium labeled PHA4400 or HDPE disks subcutaneously in a rabbit model.

| Time Months | D-PHA4400 Implant 4HB Blood Conc. (nmol/ml) | HDPE Implant Control 4HB Blood Conc. (nmol/ml) |
| --- | --- | --- |
| 0 | 10.60 ± 2.89 | 10.60 ± 2.89 |
| 1 | 11.65 ± 2.58 | 13.82 ± 2.83 |
| 2 | 10.88 ± 2.11 | 10.87 ± 3.34 |
| 3 | 8.35 ± 1.84 | 8.90 ± 0.41 |
| 4 | 5.30 ± 2.35 | 3.29 ± 2.43 |
| 5 | 4.22 ± 1.78 | 3.22 ± 0.76 |
| 6 | 4.79 ± 1.56 | 4.66 ± 2.38 |

Post implantation surgery, the concentration of [$^2$H$_6$]-4HB in the blood serum from all but one of the test animals was below the detection limit of the assay (approximately 1 nmol/ml). In one animal (rabbit 6), the concentration of [$^2$H$_6$]-4HB in the blood serum was found to be 2.52 and 1.88 nmol/ml at 1 month and 2 months post implantation, respectively. These concentrations represent 18-24% of the basal level of the natural metabolite GHB at time zero. This amount of [$^2$H$_6$]-4HB is less than the standard deviation observed in the basal level of GHB and does not cause a significant change in the total blood serum concentration of GHB (labeled and unlabeled) since the basal concentration of GHB ranged from 6.95 to 15.79 nmol/ml (10.8±2.89 nmol/ml). At 3 to 6 months post surgery, none of the animals had detectable levels of [$^2$H$_6$]-4HB in their blood serum.

TABLE 2

Serum concentration of [$^2$H$_6$]-4HB after subcutaneous implantation of D-PHA4400 or HDPE polymer disks in a rabbit model

| Rabbit ID | Implant Material | Basal (Pre-implant) | Concentration of [$^2$H$_6$]-4HB (nmol/ml) Month | | | | | |
| --- | --- | --- | --- | --- | --- | --- | --- | --- |
|  |  |  | 1 | 2 | 3 | 4 | 5 | 6 |
| 2 | D-PHA4400 | N.D. | N.D. | N.D. | N.D. | N.D. | N.D. | N.D. |
| 3 | D-PHA4400 | N.D. | N.D. | N.D. | N.D. | N.D. | N.D. | N.D. |
| 4 | D-PHA4400 | N.D. | N.D. | N.D. | N.D. | N.D. | N.D. | N.D. |
| 5 | D-PHA4400 | N.D. | N.D. | N.D. | N.D. | N.D. | N.D. | N.D. |
| 6 | D-PHA4400 | N.D. | 2.52 | 1.88 | N.D. | N.D. | N.D. | N.D. |
| 9 | D-PHA4400 | N.D. | N.D. | N.D. | N.D. | N.D. | N.D. | N.D. |
| 1 | HDPE | N.D. | N.D. | N.D. | N.D. | N.D. | N.D. | N.D. |
| 7 | HDPE | N.D. | N.D. | N.D. | N.D. | N.D. | N.D. | N.D. |

N.D.—Not detected.

Note:
Rabbit 8 was euthanized at day 28. Rabbit 9 was implanted 1 month after rabbits 1-8.

Clinical Chemistry

In addition to the blood serum analysis for 4HB and D-4HB, the serum samples were analyzed for standard clinical parameters (bicarbonate, BUN, Creat, Glucose, AST, ALT, alk phos, alb, TB, Db, and total protein). These values were unremarkable except for rabbit 6 which showed a reduced bicarbonate level (16 meq/1) at pre-implant and an elevated BUN (40 mg/dl) at 3 months post implant (Table 3). These values were attributed to a slight renal deficiency in this animal, and were judged clinically irrelevant. Notably, this animal (rabbit 6) was the only rabbit to show a measurable amount of D-4HB in its blood serum although the level of D-4HB measured was very low and near the detection limit.

TABLE 3

Clinical blood parameters of serum following implantation of D-PHA4400 or HDPE (control) measured at time 0 and at 3 months.

| | | HCO3 | BUN | Creat | Glu | AST | ALT | Alk phos | Alb | TB | Db | Total protein |
|---|---|---|---|---|---|---|---|---|---|---|---|---|
| | | | | | | | | Normal values | | | | |
| | | 22-26 meq/l | 8-25 mg/dl | 0.6-1.5 mg/dl | mg/dl | 9-40 U/L | 7-55 U/L | <200 U/L | 3.1-4.3 g/dl | Billirubin 0-1 mg/dl | Billirubin 0-0.4 mg/d | 6-8 g/dl |
| CONTROLS | | | | | | | | | | | | |
| July 19 | rabbit 1 | 24 | 17 | 0.9 | 99 | 22 | 37 | 44 | 1.6 | <0.1 | <0.1 | 5.2 |
| July 19 | rabbit 7 | 23 | 11 | 0.8 | 126 | 9 | 28 | 158 | 1.5 | 0.1 | 0.1 | 4.8 |
| AVERAGE CONTROLS | | 23.5 | 14 | 0.85 | 112.5 | 15.5 | 32.5 | 101 | 1.55 | 0.1 | 0.1 | 5 |
| Oct 25 | rabbit 1 | 22 | 22 | 1 | 108 | 22 | 51 | 20 | 1.6 | 0.1 | <0.1 | 4.9 |
| Oct 25 | rabbit 7 | 25 | 21 | 1 | 118 | 9 | 37 | 53 | 1.9 | 0.2 | 0.1 | 5.5 |
| AVERAGE | | 23.5 | 21.5 | 1 | 113 | 15.5 | 44 | 36.5 | 1.75 | 0.15 | 0.1 | 5.2 |
| poly-GHB implanted rabbits | | | | | | | | | | | | |
| July 20 | rabbit 2 | 22 | 21 | 0.9 | 122 | 10 | 23 | 59 | 1.7 | 0.1 | <0.1 | 5.1 |
| Oct 25 | rabbit 2 | 21 | 21 | 1 | 119 | 13 | 31 | 49 | 1.8 | 0.1 | <0.1 | 5.3 |
| July 20 | rabbit 3 | 19 | 17 | 1 | 122 | 20 | 34 | 301 | 1.9 | <0.1 | <0.1 | 5.7 |
| Oct 25 | rabbit 3 | 21 | 22 | 0.9 | 113 | 19 | 27 | 113 | 1.8 | 0.1 | <0.1 | 5.4 |
| July 19 | rabbit 4 | 20 | 17 | 0.7 | 103 | 20 | 34 | 97 | 1.6 | <0.1 | <0.1 | 4.8 |
| Oct 25 | rabbit 4 | 21 | 17 | 0.8 | 100 | 10 | 32 | 51 | 1.6 | <0.1 | 0.1 | 4.8 |
| July 19 | rabbit 5 | 22 | 16 | 1 | 106 | 9 | 41 | 51 | 1.6 | 0.1 | 0.1 | 4.7 |
| Oct 25 | rabbit 5 | 27 | 20 | 1 | 118 | 4 | 31 | 34 | 1.8 | 0.1 | 0.1 | 5.3 |
| July 19 | rabbit 6 | 14 | 17 | 1.2 | 108 | 20 | 17 | 69 | 1.5 | 0.2 | 0.1 | 5.1 |
| Oct 25 | rabbit 6 | 23 | 41 | 1.4 | 109 | 6 | 21 | 18 | 1.9 | 0.1 | 0.1 | 5.6 |
| rerun July 19* | rerun rabbit 6 | 16 | 19 | 1.3 | 108 | 13 | 17 | 86 | 1.7 | 0.3 | 0.1 | 5.6 |
| rerun Oct 25* | rerun rabbit 6 | 21 | 40 | 1.4 | 103 | 8 | 20 | 23 | 1.8 | 0.2 | 0.1 | 5.7 |
| Aug 19 | rabbit 9 | 24 | 18 | 1 | 108 | 15 | 42 | 79 | 1.6 | <0.1 | 0.1 | 5 |
| Oct 25 | rabbit 9 | 24 | 21 | 1 | 119 | 6 | 28 | 56 | 1.7 | 0.1 | 0.1 | 5.2 |
| Average July | rabbit 2, 3, 5, 6, 9 | 20.2 | 17.7 | 1.0 | 111.5 | 15.7 | 31.8 | 109.3 | 1.7 | 0.1 | 0.1 | 5.1 |
| Std dev July | | 3.2 | 1.6 | 0.1 | 7.6 | 4.7 | 9.1 | 87.0 | 0.1 | 0.0 | 0.0 | 0.3 |
| Average October | rabbit 2, 3, 5, 6, 9 | 22.8 | 23.7 | 1.0 | 113.0 | 9.7 | 28.3 | 53.5 | 1.8 | 0.1 | 0.1 | 5.3 |
| Std dev October | | 2.2 | 7.9 | 0.2 | 6.9 | 5.1 | 3.7 | 29.5 | 0.1 | 0.0 | 0.0 | 0.2 |

Conclusion of Bioavailability Study

Blood serum analysis of rabbits implanted with D-PHA4400 showed no significant change in the blood concentration of native 4HB compared to the control rabbits implanted with HDPE. Additionally, the blood serum concentration of D-4HB remained below the detection limit (approx. 1 nmol/ml) in all but one animal. One animal (rabbit 6) showed a detectable level of D-4HB in its blood serum at 1 and 2 months post implantation, however, the concentration was below the detection limit at 3 to 6 months in this animal and otherwise in all other animals. As such, the release of 4HB from a PHA4400 implant does not affect the native level of 4HB in the blood, nor does it accumulate in the blood.

The blood chemistry of the animals implanted with PHA4400 remained normal during the 6-month observation period. One animal (rabbit 6) showed slightly reduced level of bicarbonated and a slight elevated BUN pre-implant and at 3 months, respectively. These values were not thought to be clinically relevant as the animal's clinical blood parameters returned to normal at 4 months and the animal was otherwise healthy. In conclusion, release of 4HB from a PHA4400 implant does not adversely affect the standard clinical blood parameters measured in this study.

Since 4HB is non-toxic, released slowly from an implant, and can be readily metabolized, the amount of 4HB released from a PHA4400 implant during its degradation in the body is expected to be safe and well tolerated by the body.

The amount of D-PHA4400 implanted into each rabbit in this study was approximately 341 mg. Since the average weight of a rabbit is approximately 3 to 3.5 kg, the amount of D-PHA4400 implanted is approximately 100 mg per kg of body weight. On a per mass basis, this would be similar to implanting upwards of 6 g of PHA4400 into a person, assuming the person weighed say 60 kg. Many medical devices made from PHA4400 are expected to weigh less than 6 g, so the amount of PHA4400 used in this rabbit study is representative of a fairly massive medical device made of PHA4400.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising a polyhydroxyalkanoate (PHA) polymer obtained by a process comprising: suspending a PHA polymer biomass in ethanol for a period of time effective to extract lipids into the ethanol, separating the PHA polymer biomass from the ethanol by solid-liquid separation, collecting the ethanol-washed biomass, and extracting the PHA polymer into a solvent.

2. The composition of claim 1 wherein the polymer is precipitated with a non-solvent for the polymer, harvested, and dried.

3. The composition of claim 2, wherein the polymer does not lose more than 10% of its weight average molecular weight during recovery.

4. The composition of claim 1 wherein the weight average molecular weight of the polymer is from 50,000 to 1.2 million Da.

5. The composition of claim 1 wherein the composition is sterilized with cold ethylene oxide gas, gamma-irradiation, or electron beam irradiation.

6. The composition of claim 5 wherein the biomass is derived from a microorganism.

7. The composition of claim 1 wherein the composition is a coating for a medical device.

8. The composition of claim 1 wherein the biomass is suspended in ethanol for one hour at ambient temperature.

9. The composition of claim 1 wherein the PHA polymer is poly-4-hydroxybutyrate (P4HB) polymer.

10. The composition of claim 9 wherein the composition comprises P4HB homopolymer.

11. The composition of claim 9 wherein the endotoxin content of the composition is less than 0.22 endotoxin units (EU)/g of the composition.

12. A medical device comprising the composition of claim 1 wherein the device is selected from the group consisting of: suture, barbed suture, braided suture, monofilament suture, hybrid suture of monofilament and multifilament fibers, braids, ligatures, knitted or woven meshes, knitted tubes, catheters, monofilament meshes, multifilament meshes, patches, wound healing device, bandage, wound dressing, burn dressing, ulcer dressing, skin substitute, hemostat, tracheal reconstruction device, organ salvage device, dural substitute, dural patch, nerve guide, nerve regeneration or repair device, hernia repair device, hernia mesh, hernia plug, device for temporary wound or tissue support, tissue engineering scaffold, guided tissue repair/regeneration device, anti-adhesion membrane, adhesion barrier, tissue separation membrane, retention membrane, sling, device for pelvic floor reconstruction, urethral suspension device, device for treatment of urinary incontinence, device for treatment of vesicoureteral reflux, bladder repair device, sphincter muscle repair device, injectable particles, injectable microspheres, bulking or filling device, bone marrow scaffold, clip, clamp, screw, pin, nail, medullary cavity nail, bone plate, interference screw, tack, fastener, rivet, staple, fixation device for an implant, bone graft substitute, bone void filler, suture anchor, bone anchor, ligament repair device, ligament augmentation device, ligament graft, anterior cruciate ligament repair device, tendon repair device, tendon graft, tendon augmentation device, rotator cuff repair device, meniscus repair device, meniscus regeneration device, articular cartilage repair device, osteochondral repair device, spinal fusion device, device for treatment of osteoarthritis, viscosupplement, stent, including coronary, cardiovascular, peripheral, ureteric, urethral, urology, gastroenterology, nasal, ocular, or neurology stents and stent coatings, stent graft, cardiovascular patch, catheter balloon, vascular closure device, intracardiac septal defect repair device, including but not limited to atrial septal defect repair devices and PFO (patent foramen ovale) closure devices, left atrial appendage (LAA) closure device, pericardial patch, vein valve, heart valve, vascular graft, myocardial reneration device, periodontal mesh, guided tissue regeneration membrane for periodontal tissue, ocular cell implant, imaging device, cochlear implant, embolization device, anastomosis device, cell seeded device, cell encapsulation device, controlled release device, drug delivery device, plastic surgery device, breast lift device, mastopexy device, breast reconstruction device, breast augmentation device, devices for use with breast implants, breast reduction device, devices for removal, reshaping and reorienting breast tissue, devices for breast reconstruction following mastectomy with or without breast implants, facial reconstructive device, forehead lift device, brow lift device, eyelid lift device, face lift device, rhytidectomy device, thread lift device to lift and support sagging areas of the face, brow and neck, rhinoplasty device, device for malar augmentation, otoplasty device, neck lift device, mentoplasty device, cosmetic repair device, and device for facial scar revision.

13. The medical device of claim 12 wherein the PHA polymer is poly-4-hydroxybutyrate.

14. The medical device of claim 13 comprising a fiber wherein the fiber has a tensile strength of greater than 126 MPa or a yarn wherein the tenacity of the yarn is greater than 0.5 grams per denier.

15. A process for purifying PHA polymer from a biomass comprising suspending a PHA polymer biomass in ethanol for a period of time effective to extract lipids into the ethanol, separating the PHA polymer biomass from the ethanol by solid-liquid separation, collecting the ethanol-washed biomass, and extracting the PHA polymer into a solvent.

16. The process of claim 15, comprising suspending the biomass in ethanol for one hour at ambient temperature.

17. The process of claim 16 wherein the biomass is washed with at least 4 grams of ethanol per gram of biomass.

18. The process of claim 15 wherein the wt/wt ratio of PHA polymer biomass to ethanol is 1:1.

19. The process of claim 15, further comprising precipitating the polymer from the solvent with a non-solvent for the polymer, and drying the polymer.

20. The process of claim 19, wherein the ratio of non-solvent for the polymer to the solvent ranges from 1:2 to 4:1.

21. The process of claim 20, wherein the ratio of the non-solvent for the polymer to the solvent is 1:1.

22. The process of claim 15 wherein the solvent is selected from the group consisting of methylene chloride, chloroform, tetrahydrofuran, acetone, dioxane, ethyl acetate, dimethylene carbonate, dimethyl sulfoxide, dimethyl formamide, methyl ethyl ketone, butyl acetate, butyl propionate and diethyl carbonate, and wherein the non-solvent for the polymer is an alcohol, aqueous alcohol, or water.

* * * * *